United States Patent
Mönch

[11] Patent Number: 5,211,915
[45] Date of Patent: May 18, 1993

[54] INSTRUMENT RECEPTACLE

[75] Inventor: Harry Mönch, Knittlingen, Fed. Rep. of Germany

[73] Assignee: Richard Wolf GmbH, Knittlingen, Fed. Rep. of Germany

[21] Appl. No.: 825,360

[22] Filed: Jan. 24, 1992

[30] Foreign Application Priority Data

Feb. 2, 1991 [DE] Fed. Rep. of Germany ....... 4103146

[51] Int. Cl.$^5$ ................................................ B01L 3/00
[52] U.S. Cl. .................................... 422/102; 220/527; 220/528; 220/529; 422/99
[58] Field of Search ....................... 220/527, 528, 529; 206/363, 369, 370; 422/102, 99

[56] References Cited

U.S. PATENT DOCUMENTS

| | | | |
|---|---|---|---|
| 4,697,703 | 10/1987 | Will | 206/363 |
| 4,704,254 | 11/1987 | Nichols | 206/363 |
| 4,730,729 | 3/1988 | Moench | 206/370 |
| 4,732,187 | 3/1988 | Moench | 134/135 |
| 4,886,165 | 12/1989 | Annett | 206/370 |
| 5,011,018 | 4/1991 | Keffeler | 220/528 |
| 5,024,326 | 6/1991 | Sandel et al. | 206/370 |
| 5,098,676 | 3/1992 | Brook, Jr. | 422/102 |

FOREIGN PATENT DOCUMENTS

| | | |
|---|---|---|
| 3414679 | 10/1985 | Fed. Rep. of Germany. |
| 3436489 | 4/1986 | Fed. Rep. of Germany. |
| 3438878 | 4/1986 | Fed. Rep. of Germany. |
| 3918147 | 12/1990 | Fed. Rep. of Germany. |

Primary Examiner—James C. Housel
Assistant Examiner—Lien Tran
Attorney, Agent, or Firm—Panitch Schwarze Jacobs & Nadel

[57] ABSTRACT

A receptacle for containing preferably medical instruments and/or parts thereof is disclosed. The receptacle is for storage, disinfection or sterilization of such instruments or parts, and comprises a first trough for receiving a second trough. The troughs when nested one within the other can be closed by a detachable lid and thus combined to form a single container. The instruments are laid on flexible spiked mats which rest on point or line supports on the bottoms of the troughs and on the underside of the lid, to which mats are releasably attached.

11 Claims, 1 Drawing Sheet

INSTRUMENT RECEPTACLE

FIELD OF THE INVENTION

This invention relates to a receptacle for containing preferably medical instruments and/or parts thereof, particularly for the purpose of transport, storage, disinfection and/or sterilization of such instruments or parts, the receptacle comprising a trough provided with an insert, and a detachable lid for covering the trough and insert.

BACKGROUND OF THE INVENTION

There is disclosed in DE-B-3414679 a deep-drawn plastic receptacle having a trough part with a perforated bottom, which can be closed by means of a lid. The receptacle is for holding an ultrasonic transducer, and the trough part is provided with suitably shaped support elements and the lid with inwardly directed protuberances corresponding to said elements. The lid and trough part are releasably connectable to one another by means of snap fasteners.

DE-B-3438878 (U.S. Pat. No. 4,732,187) discloses a device for disinfecting endoscopes and accessories, which consists of a trough containing a disinfecting liquid, in which a sieve containing the parts to be disinfected can be immersed. After disinfection has been carried out, the sieve is lifted from the trough, shifted longitudinally, and then rested on lateral projections provided in the trough, so that the disinfecting liquid is drained off.

There is disclosed in DE-B-3918147 (copending U.S. patent application Ser. No. 07/513,700, filed Apr. 24, 1990) a receptacle for receiving endoscopes or parts thereof for the purpose of sterilizing or disinfecting them. The receptacle consists of a wire construction and has a bottom part with holders for the items to be treated and a top part with inwardly directed support elements, which can be releasably fastened to the bottom part. The receptacle is placed in a suitable appliance for the treatment of said items.

DE-B-3436489 (U.S. Pat. No. 4,730,729) discloses a receptacle for the dispatch, disinfection, sterilization and storage of various instruments. The receptacle has a trough which can be releasably closed by means of a lid and both the lid and the trough can be fitted with optional inserts for supporting one or more instruments in side-by-side relationship in the receptacle.

Although the receptacles described above are suitable both for containing and holding the instruments and for carrying out treatment thereof, the manufacture of such receptacles involves undesirably high production costs. Also, each different set of instruments must be assigned to a given receptacle, and the available space in the receptacle is not fully utilized, so that additional receptacles are needed for additional instruments. If a flexibly deformable holder, arranged to conform to the shape of an instrument, is used, ventilation thereof is seriously impaired. Further, if space is made available in a receptacle for a large number of instruments, the instruments will not be fixed in position, so that the instruments may be damaged when the receptacle is handled.

SUMMARY OF THE INVENTION

The present invention is intended to provide a receptacle which is capable of receiving together, for disinfection or sterilization, a large number of individual instruments and/or parts which are secured in position to provide sufficient ventilation to avoid the collection of liquid residues. The receptacle being universally usable, combinable with other receptacles, stackable and closable in a simple and reliable manner.

These ends are achieved in a receptacle of the kind to which the present invention relates by constructing the removable insert mentioned above in the form of a second trough; by providing spiked mats with projecting spikes, preferably made of silicone, which can be releasably attached to the bottom surfaces of both the first trough and the second trough as desired; and by affording the added possibility of providing the inside of the lid at least partially with spiked mats with their spikes directed towards said bottom surfaces.

The instruments or parts thereof to be treated can accordingly be accommodated and secured at two levels, the fixing of the instruments or parts at the lower level being, if required, further improved by placing an additional spiked mat over the parts at the lower level.

DETAILED DESCRIPTION OF EMBODIMENTS OF THE INVENTION

Figure 3:
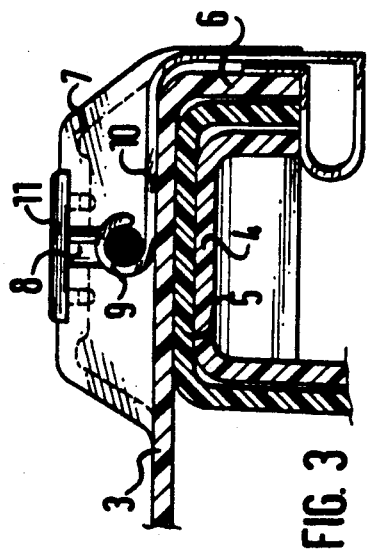
FIG. 3 is an enlarged view shown partly in section showing means for fastening the lid to the receptacle.

A receptacle according to said embodiment comprises a first trough 1 of generally rectangular shape, a second trough 2 for insertion into the first trough 1, and a lid 3. An open side of each of the troughs 1 and 2 is provided with a U-shaped profiled rim, these being referenced 4 and 5, respectively in FIG. 3. The profile of the rim 5 of the second trough 2 overlaps that of the first trough 1 circumferentially. The lid 3 is stiffened by means of a border 6 which in turn overlaps the rim 5 of the second trough 2. The lid 3 also has on each of its two minor sides, two spaced apart moulded blisters 7, each provided with a recess 8 for receiving a bearing pin 9 as shown in FIG. 3. Each pin 9 serves as a bearing for a respective U-shaped spring clip element 10 for clasping the edges of both of the troughs 1 and 2 to lock them together. By virtue of its resilient construction, the clip 10 joins the troughs 1 and 2 and the lid 3 releasably together under spring tension. In order to prevent the bearing pins 9 from falling out of the recesses 8, stoppers 11 may be provided, for closing off the recesses 8 after the clip elements 10 have been fitted. The stoppers 11 can be fixed in place by suitable snap-in locking means. The clip elements 10 have at their lower ends, handles by means of which the elements 10 can be pivoted about the pins 9 into, and out of, engagement with the lid 3.

Figure 5:
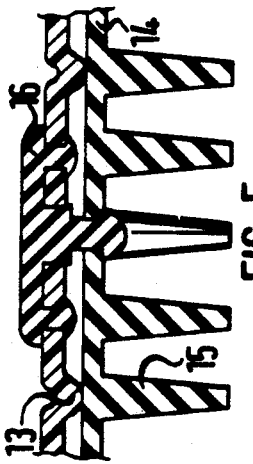
FIG. 5 is a similar view to that of FIG. 4 illustrating another way of attaching said mats within the lid.
Figure 4:
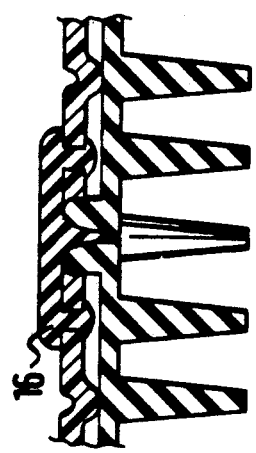
FIG. 4 is a fragmentary cross-sectional view of the receptacle illustrating one way of attaching spiked mats within the lid.
Figure 6:
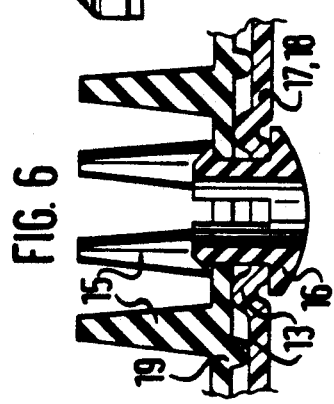
FIG. 6 is an enlarged fragmentary sectional view, showing a snap fastener for attaching a spiked mat to the lid.

The lid 3 is provided locally with recessed areas 12 formed with inwardly directed raised points or lines 13, FIGS. 4, 5 and 6, which serve as backing for spiked mats 14 placed in the recessed areas 12, for standing-off the mats 14 from the inner surface of the lid 3. Each mat 14, which has spikes 15, is attached to the lid 3 by means of a fastener 16 providing a detachable snap fastening in cooperation with corresponding raised mouldings or recesses in the spiked mat 14 (FIGS. 4, 5 and 6). Alternatively the entire inner surface of the lid 3 may be provided with a single spiked mat 14.

Figure 1:
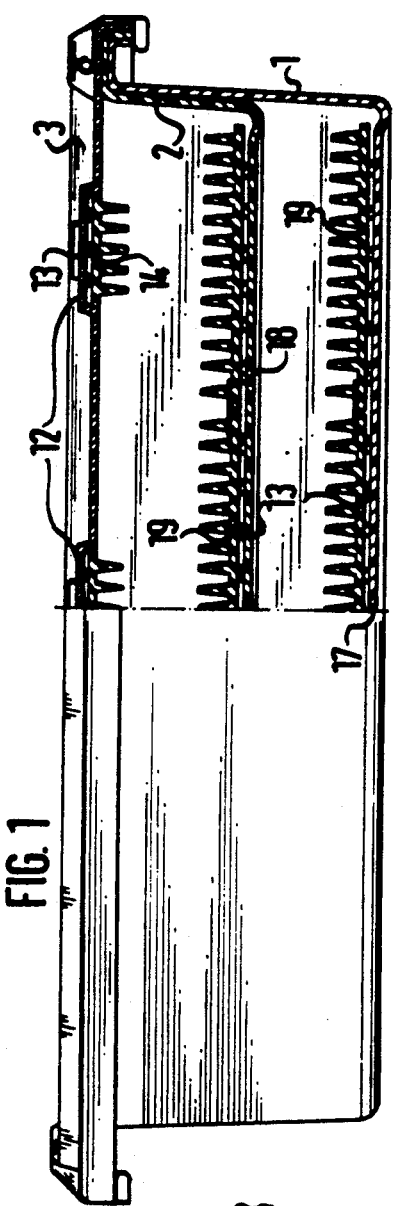
FIG. 1 is an elevational view of a receptacle according to an embodiment of the invention, shown half in longitudinal section.
Figure 2:
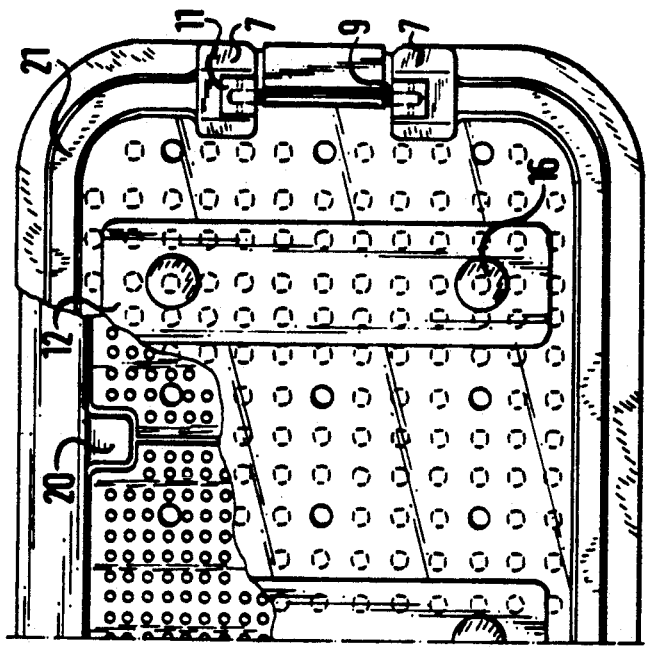
FIG. 2 is a top plan view of the part of the receptacle which is shown in section in FIG. 1, with a lid of the receptacle partially broken away.

The troughs 1 and 2 are also provided with raised points or lines 13 on their bottom surfaces 17 and 18, respectively, (FIG. 1), which points or lines serve to support further spiked mats 19 which may be fixed in position by lateral moulded blisters 20, as shown in FIG. 2, formed in the sides of the troughs 1 and 2.

Alternatively, or additionally, such raised points or lines 13 may also be provided on the mats 14 and 19 which are preferably made of silicone in order to improve their airing and drying.

Instruments to be treated by disinfection or sterilization are laid on the spiked mats 19 in the troughs 1 and 2, which have been separated. The instruments displace the spikes 15 in the region of their bearing surfaces engaged by the instruments, so that the instruments are laterally secured in the troughs by the spikes which remain undistorted outside said bearing surfaces. If need be, additional, loose spiked mats can now be laid on the instruments so placed in the trough 1, with their spikes directed towards the instruments, after which the trough 2 is inserted into the trough 1 so that the trough 2 is nested in the trough 1. The freely supported loose spiked mats are thereby pressed against the instruments in the trough 1 by the bottom 18 of the trough 2, so that the instruments are also bedded down from above between the spikes 15 of the lower mat 19. The instruments in the trough 2 are similarly bedded down, by means of the spiked mats 14 attached to the lid 3, when the lid is finally placed over the nested troughs 1 and 2 and is connected thereto by means of the clips 10 to provide a single receptacle.

For enabling a plurality of such receptacles to be stacked, the lid 3 of each receptacle may be provided with a raised rim 21 surrounding the outer surface of the lid 3, to fit the bottom 17 of the trough 1, of a superposed receptacle.

The support for the spiked mats holding the instruments, by the points or lines 13, together with the enclosure of the instruments in an array of spikes, provides for the sufficient ventilation of the instruments and thus the avoidance of the collection of liquid residues after treatment of the instruments.

What is claimed is:

1. A receptacle for containing medical instruments, including parts thereof, the receptacle comprising a first through provided with a removable insert and a detachable lid for covering the trough and the insert, wherein the insert is in the form of a second trough nested in the first trough, each trough having a bottom surface, said insert being supported above the bottom surface of said first trough, a mat releasably attached to each bottom surface, said mats having spikes projecting upwardly therefrom for supporting instruments, the lid having an inner surface, and a further mat is attached to said inner surface, said further mat having spikes projecting towards the bottom surface of said troughs.

2. A receptacle as claimed in claim 1, wherein the inside bottom surfaces of the troughs are provided with projections for supporting said mats.

3. A receptacle as claimed in claim 2, wherein said projections extend linearly across said bottom surfaces.

4. A receptacle as claimed in claim 1, wherein the bottom surfaces of said mats are provided with projections for supporting said mats on the inside bottom surfaces for said troughs.

5. A receptacle as claimed in claim 4, wherein said projections extend linearly across the bottom surfaces of said mats.

6. A receptacle as claimed in claim 1, wherein said further mats are attachable to the lid by means of fasteners.

7. A receptacle as claimed in claim 1, wherein each trough has a circumference and a U-shaped profiled rim extending therearound, said rims being shaped on that the rim of the second trough overlaps the rim of the first trough around the circumference thereof.

8. A receptacle as claimed in claim 7, wherein the lid has a border overlapping both of said rims.

9. A receptacle as claimed in claim 8, wherein the lid is provided with spring clip elements for attaching the lid to at least one of said troughs by clasping the U-shaped rim thereof.

10. A receptacle as claimed in claim 9, wherein the spring clip elements are pivotable into, and out of, engagement with said U-shaped rim.

11. A receptacle as claimed in claim 1, wherein the lid has a circumference and a raised rim therearound, whereby the bottom of the first trough of a further and similar receptacle may be stacked thereon.

* * * * *